United States Patent
Seip et al.

(10) Patent No.: US 10,258,313 B2
(45) Date of Patent: Apr. 16, 2019

(54) MICROBUBBLE SIGNAL BASED TEMPORAL-BONE THICKNESS COMPENSATION FOR SONOTHROMBOLYSIS

(71) Applicant: KONINKLIJKE PHILIPS N.V., Eindhoven (NL)

(72) Inventors: Ralf Seip, Carmel, NY (US); William Tao Shi, Wakefield, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/534,092

(22) PCT Filed: Dec. 1, 2015

(86) PCT No.: PCT/IB2015/059229
§ 371 (c)(1),
(2) Date: Jun. 8, 2017

(87) PCT Pub. No.: WO2016/092414
PCT Pub. Date: Jun. 16, 2016

(65) Prior Publication Data
US 2017/0360406 A1    Dec. 21, 2017

Related U.S. Application Data

(60) Provisional application No. 62/090,701, filed on Dec. 11, 2014.

(51) Int. Cl.
A61B 8/08    (2006.01)
A61B 8/00    (2006.01)
(Continued)

(52) U.S. Cl.
CPC .............. *A61B 8/481* (2013.01); *A61B 8/085* (2013.01); *A61B 8/0808* (2013.01); *A61B 8/54* (2013.01);
(Continued)

(58) Field of Classification Search
CPC . A61B 8/0808; A61B 8/481; A61B 17/22004; A61B 2017/22008;
(Continued)

(56) References Cited

U.S. PATENT DOCUMENTS 6,302,845 B2    10/2001    Shi et al.
2007/0016050 A1*    1/2007    Moehring ................ A61B 8/06
600/454

(Continued)

FOREIGN PATENT DOCUMENTS

WO    2010103469 A1    9/2010

*Primary Examiner* — Jennifer Dieterle
*Assistant Examiner* — Vani Gupta

(57) ABSTRACT

An ultrasonic intracranial sonothrombolysis pressure amplitude is pre-quantified by using an ultrasound-scanner control unit (110) having an increasing and/or decreasing mode and designed for: with respect to a current mode, interrogating a blockage site iteratively so as to progressively and respectively increase or decrease a pressure amplitude of ultrasound being emitted to the site at which bubbles (144) for oscillating that is caused by the emitted ultrasound are present; iteration to iteration, deriving, from echoes of the emitted ultrasound, a magnitude of an energy of a signal; and automatically identifying, for the quantifying, an iteration that, in comparison with a just-previous iteration, fails to increase the magnitude. The interrogating may span a region that contains or goes through: the obstruction; another part of the blood vessel; and bubble circulation within a neighboring vessel and a neighboring capillary (136). The deriving can be based on an ultraharmonic signal, with band-pass filtering being utilized to extract the ultraharmonic signal (Continued)

from returning signals differenced to remove stationary content.

11 Claims, 7 Drawing Sheets

(51) Int. Cl.
   *A61B 17/22* (2006.01)
   *A61N 7/00* (2006.01)
   *A61B 17/225* (2006.01)

(52) U.S. Cl.
   CPC .......... *A61B 17/22004* (2013.01); *A61N 7/00* (2013.01); *A61B 8/587* (2013.01); *A61B 17/2256* (2013.01); *A61B 2017/22008* (2013.01); *A61N 2007/0039* (2013.01); *A61N 2007/0052* (2013.01)

(58) Field of Classification Search
   CPC ....... A61B 8/085; A61B 8/54; A61B 17/2256; A61B 8/587; A61N 2007/0039; A61N 7/00; A61N 2007/0052
   See application file for complete search history.

(56) References Cited

U.S. PATENT DOCUMENTS

| | | | |
|---|---|---|---|
| 2012/0083718 A1* | 4/2012 | Alleman | A61N 7/00 601/2 |
| 2012/0130288 A1* | 5/2012 | Holland | A61B 8/06 601/2 |
| 2012/0165670 A1* | 6/2012 | Shi | G01S 7/52049 600/442 |
| 2013/0006106 A1 | 1/2013 | O'Reilly et al. | |
| 2014/0147013 A1* | 5/2014 | Shandas | A61B 8/481 382/107 |

* cited by examiner

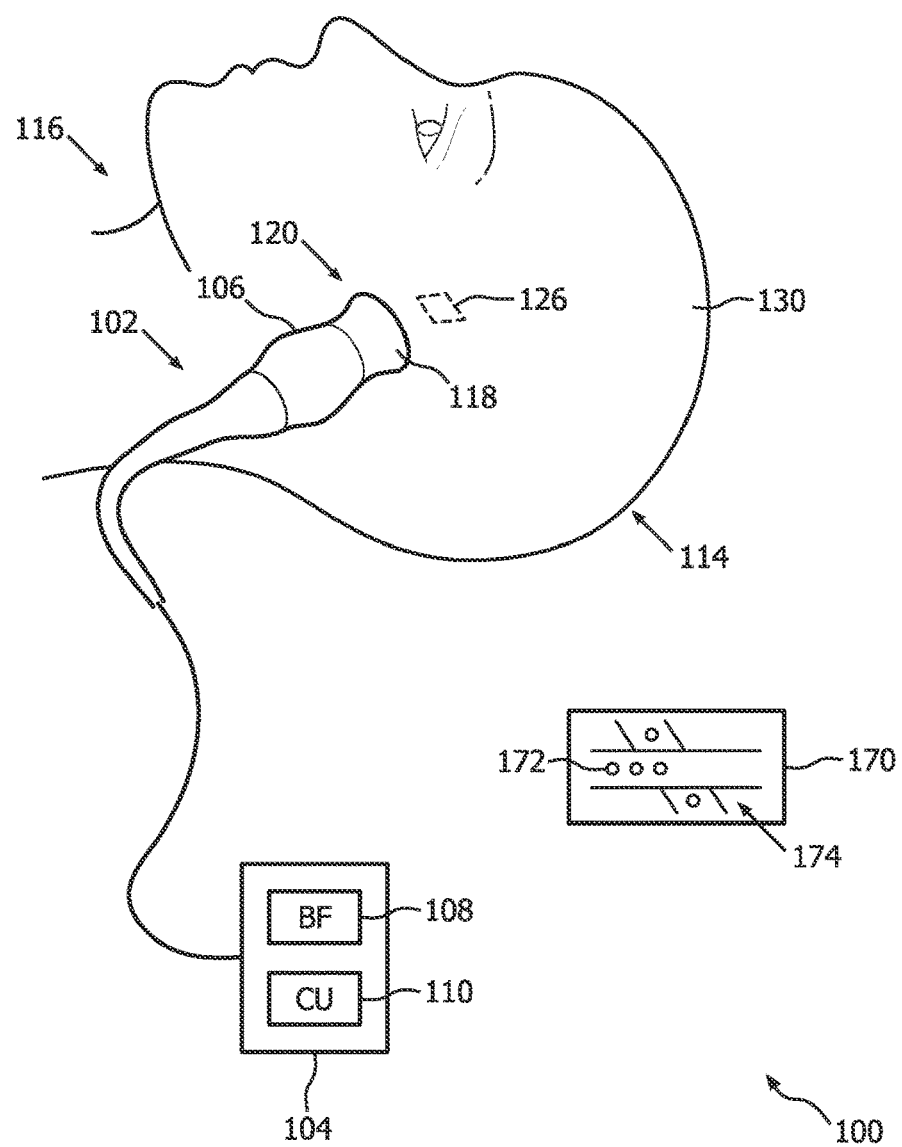
FIG. 1-I

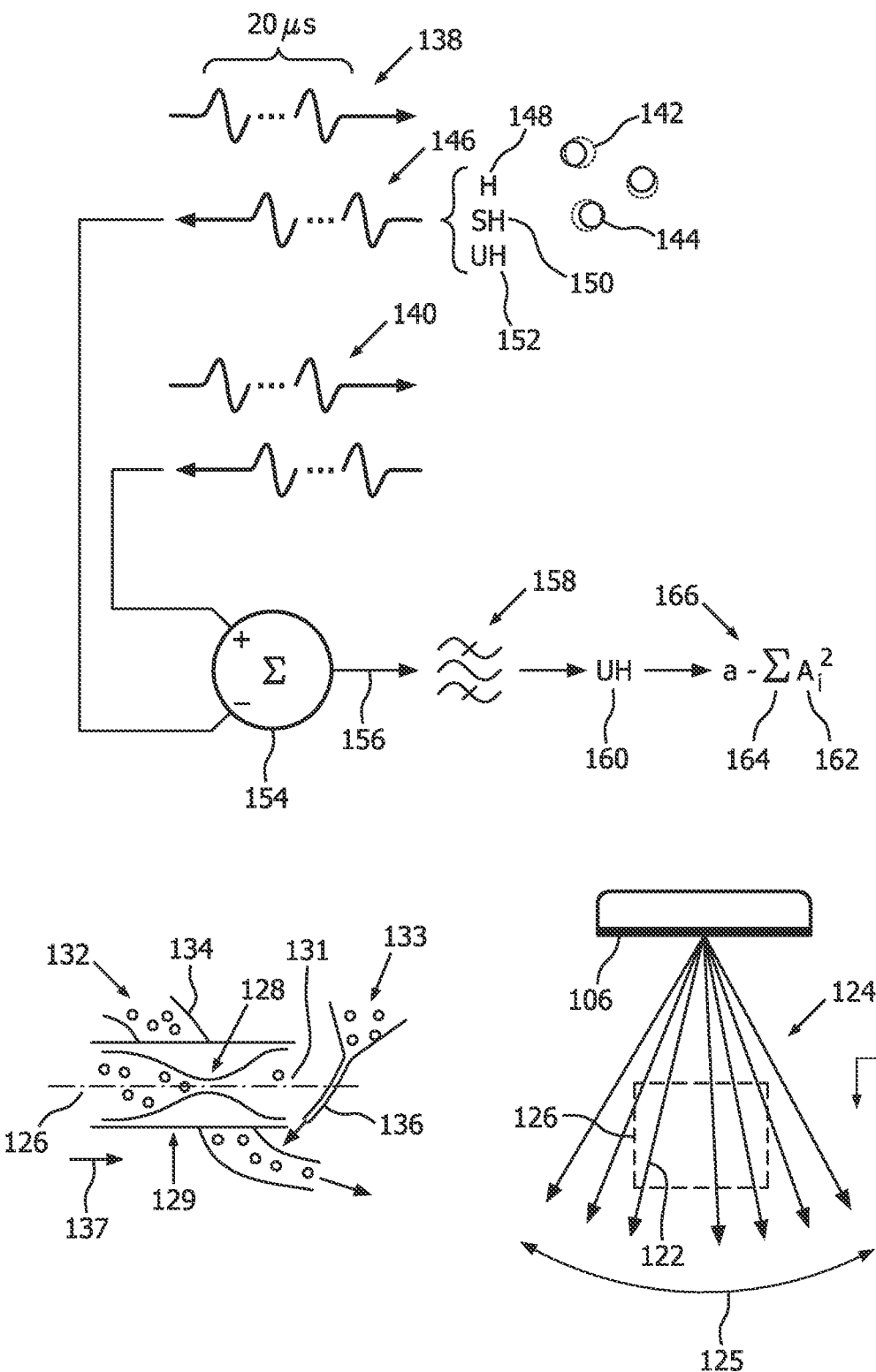
FIG. 1-II

MICROBUBBLE SIGNAL BASED TEMPORAL-BONE THICKNESS COMPENSATION FOR SONOTHROMBOLYSIS

This application is the U.S. National Phase application under 35 U.S.C. § 371 of International Application No. PCT/IB2015/059229, filed on Dec. 1, 2015, which claims the benefit of U.S. Provisional Application Ser. No. 62/090,701, filed Dec. 11, 2014. These applications are hereby incorporated by reference herein.

FIELD OF THE INVENTION

The present invention relates to quantifying an ultrasound dose for sonothrombolysis and, more particularly, to such quantifying based on a preparatory stage of ultrasound feedback.

BACKGROUND OF THE INVENTION

Sonothrombolysis (STL) treatments for acute stroke rely on ultrasound energy (targeting the clot) delivered through the temporal bone and microbubbles injected systemically to achieve clot dissolution and vessel recanalization.

Sonothrombolysis treatments are being investigated by a multitude of researchers and clinicians for their potential role in treating acute stroke. In STL treatments, ultrasound pulses are delivered through the skull temporal bone, targeted at the clot that causes the occlusion. Microbubbles, an ultrasound contrast agent, are introduced into the bloodstream, as their mechanical oscillation at the clot site due to the applied ultrasound energy has been shown to over time dissolve the clot and achieve vessel recanalization for acute stroke treatment. One of the advantages of STL treatments is that they can be performed without the use of drugs (such as t-PA, or tissue plasminogen activator, a common "clot-busting" drug), which carry with them significant restrictions to their use, and overall low treatment success. Circulating microbubbles (which are utilized for the STL treatment), oscillate differently when subjected to different amplitude ultrasound pulses. Such oscillation at higher ultrasound pressures is termed cavitation, which actually emits ultrasound energy as part of this process at many different frequencies (harmonic, subharmonic, and ultraharmonic frequencies), which can be detected.

One challenge associated with STL treatments is that the ultrasound energy is delivered to the clot location inside the patient's brain through the skull. Several acoustic windows are available in the skull that allow ultrasound energy to be transmitted into the brain. For STL, the best acoustic window is the temporal bone, located at the sides and base of the skull, as most strokes occur due to the occlusion of the middle cerebral arteries, which are located behind the temporal bone, and can be visualized with diagnostic ultrasound and color Doppler. Even so, the temporal bone attenuates ultrasound significantly, degrading the ability to image the brain, and also making it more difficult to deliver the required ultrasound energies for successful STL treatments. On average, ultrasound pressures are reduced by 12 dB (75%) by the temporal bone at the 1.6 to 2 MHz frequencies typically being used for STL. This is a significant amount.

Another challenge associated with STL treatments is that the thickness and consequent attenuation of the temporal bone vary from patient to patient, potentially resulting in either higher or lower ultrasound energies being delivered to the clot location, with the potential of causing undesired bioeffects (in the case of a thinner temporal bone yielding higher ultrasound pressures in the brain), or not being able to dissolve the clot at all (in the case of a thicker temporal bone yielding lower ultrasound pressures in the brain).

SUMMARY OF THE INVENTION

Proposed herein below are a novel non-invasive method, device, and software to compensate the ultrasound amplitude (i.e. by either increasing or decreasing it), so that the clot is always being insonified by the correct ultrasound pressure to achieve reliable clot dissolution and vessel recanalization, regardless of the attenuation characteristics of the patient's temporal bone. This technological solution exploits a characteristic behavior of microbubbles and their ultrasonic imaging signature when subjected to varying pressure ultrasound pulses. This behavior, which the instant inventors discovered, is, as described further below, virtually independent of microbubble concentration (in circulation), as well as blood circulation speed, thus requiring no a priori knowledge of the brain's perfusion characteristics and patient anatomy, nor requiring any other type of specific calibration. This makes compensating for the temporal bone thickness possible in a simple, non-patient-specific way that does not require calibration, and is independent of the patient-specific physiology. This simplifies implementation and allows for wide deployment.

The temporal bone compensation can be accomplished by a single ultrasound transducer, thus simplifying the overall STL device design, and potentially allowing implementation on existing ultrasound systems/scanners.

Data for compensation is non-invasively acquired over a large region of interest that contains the clot, occluded vessels, and non-occluded neighboring vessels and capillaries with circulating microbubbles. The estimate is thus robust against tissue heterogeneity.

The technique eliminates the need for any patient-specific a priori information, and does not require patient-specific calibration, both of these factors simplifying implementation and allowing wide deployment.

What is proposed herein below affords a methodology, device, and a computer-readable product that are independent of several treatment parameters that are difficult to impossible to control. One is microbubble concentration in the treatment region. Microbubble concentration can be estimated systemically, but is difficult to determine locally due to the presence of the occluding clot, local vasculature, etc. Other parameters relate to blood flow dynamics in the treatment region.

The innovative technique quantifies the ultrasound dose that allows for clot dissolution while not causing any additional detrimental bioeffects.

In accordance with what is proposed herein below, a particular ultrasound excitation sequence is utilized to infer the attenuation of the temporal bone. Once this information is known, the ultrasound energy/pressure amplitude can be increased/decreased to compensate for it, as required.

In an aspect of what is proposed, an apparatus is configured for, with respect to obstructed flow in a lumen within a brain, bubbles being located at a site of the obstruction, quantifying a pressure amplitude of ultrasound to be applied to, via bubble oscillation, alleviate the obstructed flow. The apparatus includes an ultrasound-scanner control unit that infers the attenuation of the temporal bone, the control unit being, for this purpose, configured with an increasing mode and/or a decreasing mode and configured for: with respect to a current mode, interrogating the site iteratively so as to progressively and respectively increase or decrease a pressure amplitude of ultrasound being emitted to the site at which bubble oscillation is being caused by the emitted ultrasound; iteration to iteration, deriving, from echoes of the emitted ultrasound, a magnitude of an energy of a signal; and automatically identifying, for the quantifying, an iteration that, in comparison with a just-previous iteration, fails to increase the aforementioned magnitude.

Details of the novel technology for intracranial sonothrombolysis ultrasound-dose pre-quantification are set forth further below, with the aid of the following drawings, which are not drawn to scale.

BRIEF DESCRIPTION OF THE DRAWING

FIG. 1 is a schematic and conceptual diagram providing an overview of an exemplary system in accordance with the present invention;

DETAILED DESCRIPTION OF EMBODIMENTS

Figure 2A:
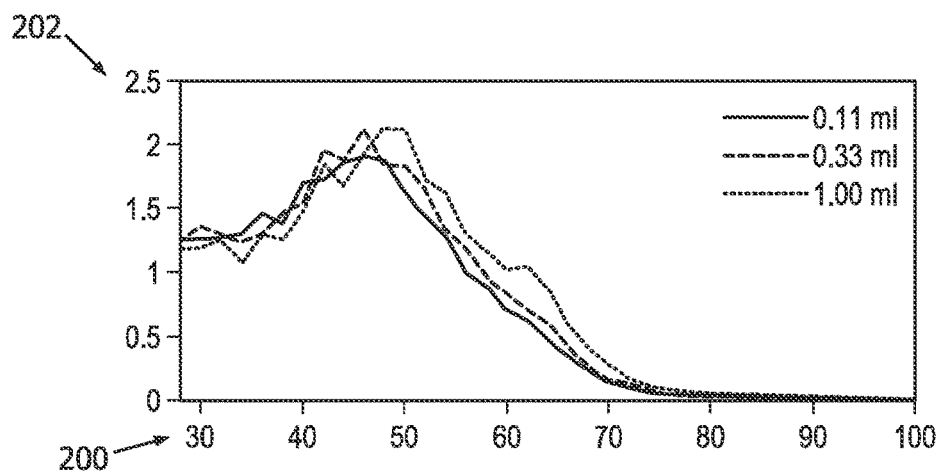
FIGS. 2A-2C are test results in accordance with examples of the present invention.

An ultrasound-based intracranial sonothrombolysis (STL) treatment and ultrasound-dose pre-quantification apparatus 100 is depicted by way of illustrative and non-limitative example in FIG. 1.

The apparatus 100 includes an ultrasound scanner 102 which further includes a console 104 and an imaging and therapy ultrasound probe 106. The console 104 includes a transmit and receive beamformer 108, and an ultrasound-scanner control unit 110. The console 104 will typically include other components, such as interactive user controls and a display, both of which are not shown. Incorporated within the console 104 is control logic, such as one or more integrated circuits and in any combination of software, hardware, and firmware.

The apparatus further comprises a head frame, head cap, headband, or headset, (not shown) for securing the probe 106 against a head 114 of a medical treatment recipient 116, such as a patient diagnosed with acute ischemic stroke. Such headpieces for intracranial examination and therapy are well-known, and are disclosed, for example, in commonly-assigned U.S. Patent Publication Nos. 2012/0165670 and 2010/0160779 to Shi et al. and Browning et al., respectively.

The probe 106 may include a single wideband ultrasound transducer 118 for both ultrasound dose pre-quantification and dose delivery, thus potentially allowing implementation of existing ultrasound systems or scanners. The transducer 118 is secured against a temporal bone 120 of the head 114 by the force the headset applies in affixing the probe 106 to the temple. The temporal window with the shorter distance to the clot is chosen. The clot-induced occlusion and/or ischemic region may be located using computed tomography (CT), magnetic resonance imaging (MRI), or ultrasound as with the same probe 106. Alternatively, separate transducers to the same temple 120, as in a concentric side-by-side arrangement, may be provided, one for the pre-quantification/preparatory stage, and optionally a preceding parameter-determination stage, and the other for the therapy stage.

As another alternative, separate probes with corresponding examination and therapy transducers may be used in series ipsalaterally. Whether for examination and/or therapy, the transducer 118 can consist of a one-dimensional phased array of transducer elements. For volumetric interrogation, a two-dimensional matrix array can be employed. Likewise, this type of an array can be employed for therapy.

In a microbubble excitation mode which is used prior to medical treatment, the probe 106 is used for a sector scan consisting of serially performed line scans in multiple directions 122. The excitation mode is used both in a preparatory phase with the patient present, and optionally is a preceding parameter-determination phase discussed further below. Multiple ultrasound pulses are issued in series for each line scan. For example, 20 directions 122 are utilized in a sector pattern 124 having an angular span 125 of 60 degrees, with at least two pulses per direction. As another example, the angular span 125 utilized can be any value within the range from 40 to 80 degrees. The multiple directions 122 collectively cover a region of interest (ROI) 126 which is planar and thus has a depth, although the technique can be expanded for covering a volume of interest. The ROI 126 is made large enough that it contains or goes through each of: an obstruction 128 of a lumen 129, such as a blood vessel, of the brain 130 within the patient's head 114; another part 131 of the blood vessel 129; bubble circulation 132 within a neighboring vessel 134; and bubble circulation 133 within what, with respect to the blood vessel 129, is a neighboring capillary 136. As seen in FIG. 1, in a blood flow direction 137, the flow in the blood vessel 129 is largely obstructed, as evidenced by the vessel narrowing and the sparsity of microbubbles just downstream. Alternatively, the obstruction could be total.

A specific excitation sequence, different from the STL treatment sequence, is used to generate input data for temporal bone compensation. Signal processing removes the tissue signal, leaving only the microbubble cavitation signal. Energy of an ultraharmonic of the latter signal is computed, that latter signal being a function of shove-described excitation mode.

More specifically, the excitation sequence includes, in each of the multiple directions 122 of the sector pattern 124, at least two "color Doppler" querying pulses, or similar pulses, 138, 140. Each pulse 138, 140 is 10 to 40 μs (microseconds) in length 206. The top pulse 138 shown in FIG. 1 is, for example, a 32 cycle pulse that is 20 μs long at 1.6 MHz. The pulse 138 is followed by a listening period, e.g., 60-100 μs long, with a length that is dependent upon imaging depth. The pulse 138 causes oscillation 142 of microbubbles 144 in the ROI 126. The resulting, returning cavitation signal 146 contains harmonic 148, sub-harmonic 150, and ultraharmonic 152 frequency components. The cavitation signal 146 is acquired during the listening period. In the sector scan, one signal 146 is acquired for each emitted, querying pulse 138, 140. An excitation pressure amplitude, or "excitation pulse amplitude", of the querying pulses 138, 140 is kept constant throughout the sector scan. Although, as will be discussed further below, the excitation pressure amplitude is varied from sector scan to sector scan.

The querying pulses 138, 140 of a given direction 122 are paired, one pulse being subtracted 154 from the other. This operation removes the tissue signal which is stationary, thereby leaving only a microbubble-specific cavitation signal 156.

Band-pass filtering 158 yields an ultraharmonic signal 160. The filter is centered at an ultraharmonic frequency which is 1.5 times the center frequency of the pulses 138 and 140 used in the microbubble excitation mode.

Squared values, i.e., amplitudes 162 or pressure values, of the signal 160 are summed 164 in a computation of an energy 166 of the signal.

Thus, for each of the multiple directions 122, a local ultraharmonic energy 166 is calculated. The local ultraharmonic energies 166 are averaged to yield a global ultraharmonic energy signal.

The above excitation mode and ultraharmonic computation have been implemented in an iE33 ultrasound scanner. An excitation pulse amplitude 200 of querying pulses 138, 140 of a respective sector scan is controlled by the acoustic output parameter 'Atten'. The higher Atten is, the lower in pressure amplitude the ultrasound excitation pulse is.

To verify the utility of this approach, several in-vitro experiments were carried out with a flow phantom 170, in which microbubbles 172 at a certain concentration were circulated at a constant flow rate, while the phantom (made of tissue-mimicking material) and vessels 174 were being imaged and subjected to the excitation pulses of increasing pressure amplitude with each sector scan is a series of such scans. The flow phantom 170, as discussed further below, is optionally used in a parameter-determination phase independent of any patient in which measurements can be made to position the applied ultrasound pressure locally during treatment to any targeted or desired safe and effective level.

The FIG. 2A shows a global ultraharmonic energy signal 202 computed as a function of the excitation pulse amplitude 200 (via 'Atten') at three different microbubble concentrations. Notably, that the higher the excitation pulse (lower value for Atten), the higher the energy level of the ultraharmonic, up to approximately Atten 48. After this value, the energy level of the ultraharmonic decreases.

The overall shape of the ultraharmonic energy 202 as a function of the amplitude 200 of the excitation pulse is largely independent of microbubble concentration, as indicated by the 3 microbubble concentration levels tested (0.11 milliliters per liter (ml/l), 0.3 ml/m, 1 ml/l).

This is an important characteristic, as the microbubble concentration in the brain region in which the clot/target zone/treatment area will be located is unknown. The flow rate of 125 ml/min was kept constant for all 3 different microbubble concentrations.

Figure 2B:
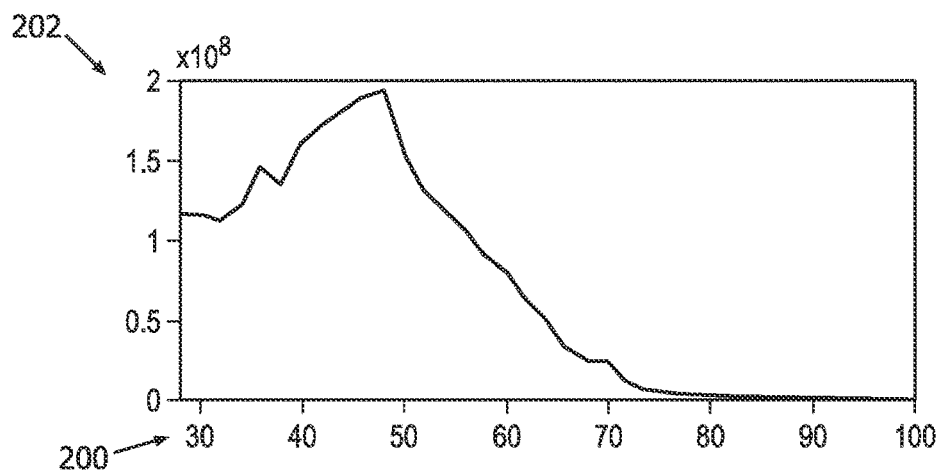

FIG. 2B shows the global ultraharmonic energy signal 202 computed as a function of the excitation pulse amplitude 200 (via 'Atten'). While the flow rate of FIG. 2A was kept at 125 milliliters per minute (ml/min), FIG. 2B shows the global ultraharmonic energy signal 202 with a flow rate of 50 ml/min.

Again it is noted that the behavior of the global ultraharmonic energy signal 202, and the overall characteristics of the curve seem to be independent of yet another parameter, the flow rate.

This is important, as the microbubble flow rate in the brain region in which the clot/target zone/treatment area will be located is unknown. The microbubble concentration was kept constant for the 2 different flowrates.

Figure 2C:
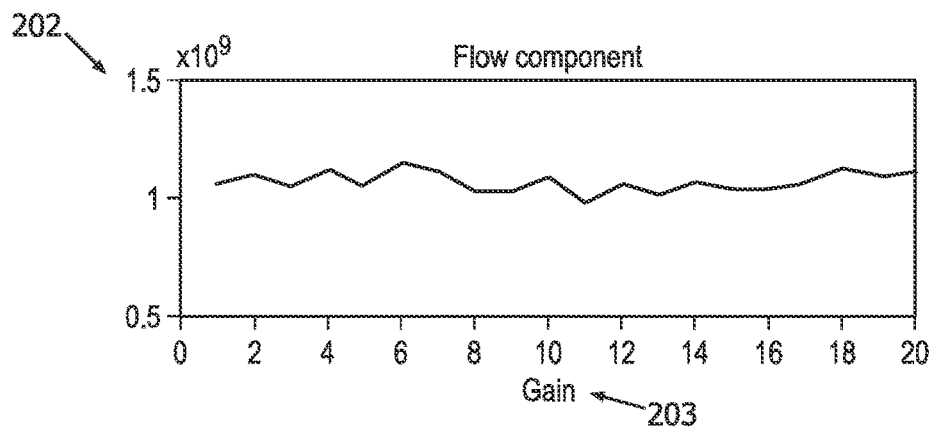

FIG. 2C shows the global ultraharmonic energy signal 202, this time computed as a function of ultrasound scanner gain 203. It is seen that for a given flow rate and microbubble concentration, the estimate is independent of the settings of the scanner 102, which is again an important requirement.

As mentioned herein above, the excitation amplitude 200 is, in microbubble excitation mode, varied from sector scan to sector scan. This is done to find the peak in FIGS. 2A and 2B, which corresponds to the maximum of the global ultraharmonic energy signal 202 over all excitation amplitudes 200. In other words, "the maximum global ultraharmonic energy signal 202 (MGUE)" is always found at a fixed excitation pulse amplitude 200 of Atten 48 in the given flow phantom 170. Because the ultrasound attenuation of the tissue-mimicking material between the transducer surface and the flow tube 174 (where insonated microbubbles 172 oscillate) inside the tissue-mimicking material can be measured and thus is known, the "particular" local ultrasound pressure responsible for locally exciting bubbles (to reach the MGUE at Atten 48) inside the flow tube is an unique constant and may simply be called as "the MGUE in situ acoustic pressure."

It should be pointed out that "the MGUE in situ acoustic pressure" can be determined using the above-mentioned flow phantom setup and experimental procedures.

"The MGUE in situ acoustic pressure" is considered unique for a particular type of contrast microbubbles insonified as a particular ultrasound frequency, independent of the microbubble concentration (FIG. 2A), flow velocity (FIG. 2B) as well as scanner reception parameters such as the scanner gain (FIG. 2C).

During ultrasound propagation from the transducer surface (also, the body surface) to a region of interest (ROI) inside the human body, the attenuation between the transducer surface and the ROI is usually unknown.

The uniqueness of "the threshold in situ acoustic pressure" can be used for the determination of the attenuation:
  A. One can set the local acoustic pressure inside the ROI to be the known "MGUE in situ acoustic pressure" by adjusting (increasing or decreasing) the scanner power output (i.e., the excitation pulse amplitude 200) to allow it to reach the maximum for the global ultraharmonic energy signal that is only scattered from bubbles located within the ROI.
  B. The attenuation is estimated as the ratio of the known final acoustic pressure at the transducer surface to "the MGUE in situ acoustic pressure" inside the ROI.

Once the attenuation encountered in therapy in this way is determined, the excitation amplitude for achieving any desired in situ acoustic pressure is readily computed. The above-described adjusting of the scanner output power, iteratively done sector scan to sector scan, is optionally done with the flow phantom 170 in a parameter-determination phase prior to involving the patient 116. However, it is later performed in the preparatory phase while insonifying the patient 116 pre-treatment.

In these contexts and in some embodiments, the excitation amplitude 200 is progressively increased sector scan to sector scan. When the global signal 202 of the current iteration, i.e., sector scan, does not exceed that of the just-previous iteration, a stopping point has been reached. Then, for instance, when in the preparatory phase, if the current, or just-previous, excitation amplitude 200 corresponds to an "MGUE in-situ acoustic pressure" of e.g., 0.8 MPa, at the obstruction 128, the excitation amplitude 200 from the scanner is then reduced by half so that the STL treatment can be performed with the respective treatment pressure at 0.4 MPa. Thus, the treatment amplitude may be based proportionally on the current or just-previous excitation amplitude 200. Although, since the current and just-previous excitation amplitudes 200 are, by virtue of the intervening increment, based on each other, the treatment amplitude may be characterized as based on either excitation amplitude.

The increase in the excitation amplitude 200 during the excitation mode can be linear or exponential. The linear increase protocol can be continued during the entire excitation mode, so that the increases are in equal increments.

However, in other embodiments, the excitation amplitude 200 is progressively decreased, to find the peak from the other side of the peak.

In some embodiments, there is an increasing mode 204 in which excitation amplitude 200 is progressively increased, and a decreasing mode 208 in which excitation amplitude is progressively decreased, the switching of one mode to the other being selectable. These two modes will, at times, be referred to herein below collectively as the inc/dec mode 204, 208 which may each be set, at any given time, either to increasing or to decreasing.

Figure 2D:
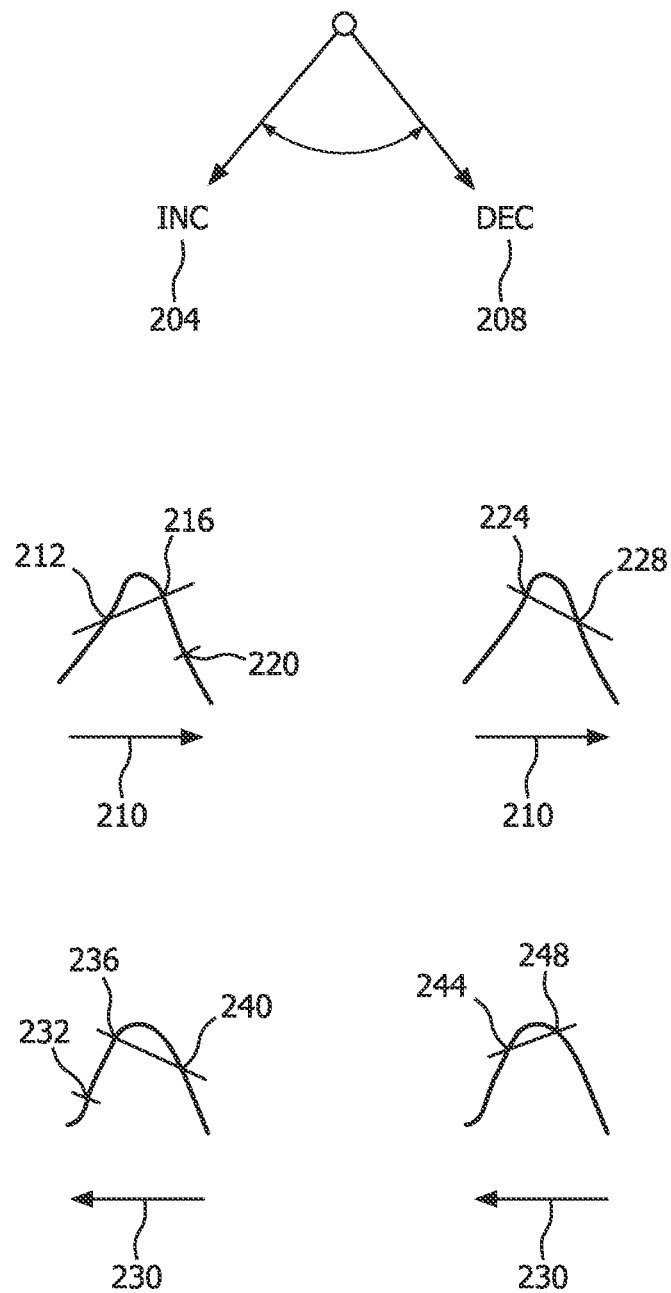
FIG. 2D is a conceptual diagram of ultrasound emission and response exemplary of aspects of the present invention.

With reference to FIG. 2D, fine tuning of peak detection, when implemented or selected, can involve switching of modes 204, 208 in the course of the fine tuning.

With further reference to FIG. 2D, three consecutive sector scans are, while in the increasing mode 204 as shown by the arrows 210, made which yield correspondingly three global ultraharmonic energies 212, 216, 220. The increment sizes are exaggerated in FIG. 2D for simplicity of demonstration. Since the middle energy 216 exceeds that of the previous iteration, the stopping criterion has not been met. In the next iteration, the final energy 220 does not exceed that of the previous iteration, and so that stopping criterion has been met. However, the peak has been bypassed.

Similarly for the two global ultraharmonic energies 224, 228, the current iteration has bypassed the peak, while the just-previous iteration has not reached the peak.

Thus, although the stopping criterion has been met by virtue of the second energy 228 not exceeding the first energy 224, the peak determination is coarse.

The exact analog in the decreasing mode 208 as shown by the arrows 230, is shown for the respective global ultraharmonic energies 232-248.

A relatively coarse determination is usable, because the peak represents an excitation amplitude that is not to be exceeded, or at least maintained, and an operational pressure amplitude for treatment can safely be made much lower.

The determination can be improved by making the increments finer; however, this is in trade-off with a longer convergence time which is particularly to be avoided in the preparatory phase which occurs with and involves the patient 116.

One example of the fine tuning option is to, upon reaching the stopping criterion, fall back to the amplitude of the just-previous iteration. This latter amplitude corresponds to the middle energy 216 in FIG. 2D. At this point, a single iteration can be performed in the same increasing mode 204 with a smaller increment. If the single iteration results in a decrease in the energy 202, the mode 204 is switched to the decreasing mode 208. The progressive testing then continues in the switched-to mode 208 with the same smaller decrement. If, on the other hand, the single iteration, as in the case of the energies 224, 228, results in an increase in the energy 202, the progressive testing then continues in the same increasing mode 204 with the same smaller increment.

Another fine-tuning option is to forego falling back to the just-previous iteration. Instead, upon reaching the stopping point, the mode 204, 208 can be switched and the progressive iterations can continue with a smaller increment/decrement.

Treatment ultrasound is then, automatically and seamlessly in some embodiments, applied at a pressure amplitude based on, and no larger than, the pressure amplitude quantified in the preparatory phase or specifically by the fine tuning.

An exemplary algorithm 300 providing more detail and generalized for a number of different cases is presented in the following flow charts 3A-3C.

Figures 3A, 3B:
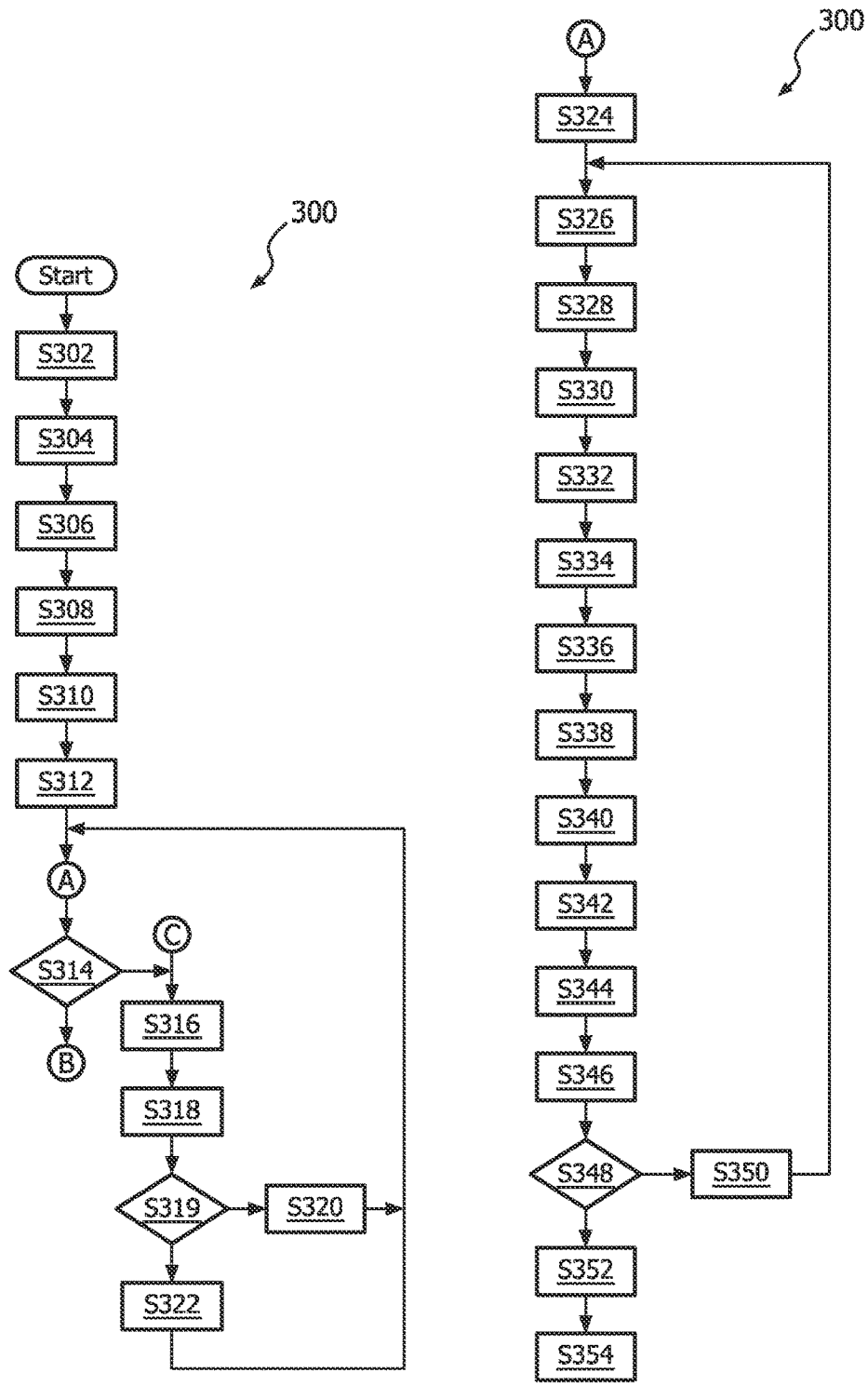
FIGS. 3A-3C are flow charts providing examples of operations in carrying out a method in accordance with the present invention.

Referring to FIG. 3A, the transducer 118 is affixed to the temple bone 120 of the patient 116 (step S302). The occluded region containing the obstruction 128 is located (step S304). The microbubble infusion is started (step S306). The injection of fluid in which the microbubbles are suspended can be accomplished by means of a pump feeding an intravenously placed catheter. Alternatively, the solution can be manually injected directly using a syringe. The ROI 126 may then be selected (step S308), interactively utilizing the user controls and the display. A number of values of the algorithm 300 are initialized (step S310), including a running sum of direction-specific energy measurements; the current dec/inc mode 204, 208; the current inc/dec size or formula; the current excitation amplitude (EA) 200; the number of directions 122; and the angular spacing of the directions. Some variables are cleared (step S312), such as the previous EA and the current and previous global ultraharmonic energies (GUEs). Next, a subroutine A is executed, which is detailed in FIG. 3B. Subroutine A executes a sector scan. Then, if, based on the sector scan, the current GUE exceeds the previous GUE (step S314), the previous EA is set equal to the current EA (step S316). Likewise, the previous GUE is set equal to the current GUE (step S318). If the current inc/dec mode is the increasing mode 204 (step S319), the EA is incremented (step S320). Otherwise, if the current inc/dec mode is not the increasing mode 204 (step S319), it is the decreasing mode 208, and the EA is decremented (step S322). In either case, return is made to the subroutine A execution step that follow step S312. If, on the other hand, the current GUE does not exceed the previous GUE (step S314), then, via entry point B, the flow in FIG. 3C is executed.

Referring now to FIG. 3B, i.e., subroutine A, processing points in the first direction 122 (step S324). The first querying pulse 138 issues (step S326). The cavitation signal 146 echoed back is received (step S328). The cavitation signal 146 is recorded (step S330). The second querying pulse 140 issues (step S332). The cavitation signal 146 echoed back is received (step S334). The difference between the two cavitation signals 146 is computed (step S336). The difference signal is band-pass filtered (step S338) to extract the ultraharmonic signal. The amplitudes of the extracted signal in the depth direction are squared (step S340). The squares are summed (step S342). The signal energy is computed based on the sum (step S344). The computed energy is added to a running sum (step S346). If the current direction 122 is not the last direction (step S348), the current direction is incremented (step S350) and return is made to the querying pulse issuing in step S326. Otherwise, if the current direction 122 is the last direction (step S348), the running sum is divided by the number of addends in deriving the current GUE (step S352). Both the current GUE and the current EA are stored (step S354).

Figure 3C:
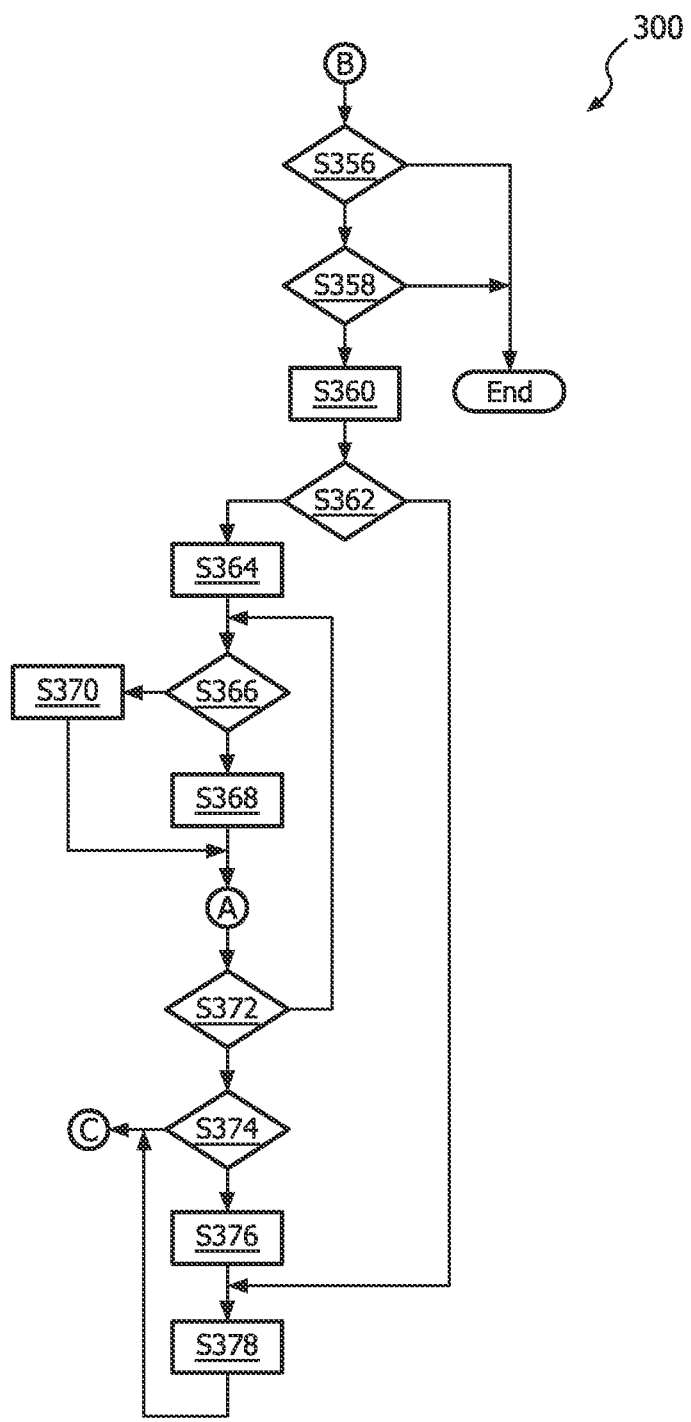

Referring now to FIG. 3C, if quantifying is not to continue since fine tuning is not to be done (step S356) or if quantifying is not to continue due to fine tuning being deemed sufficiently complete (step S358), the algorithm 300 ends, and a treatment amplitude can be determined based on the results of the algorithm. Otherwise, if fine tuning is to proceed (steps S356, S358), the size of the increment if in the increasing mode 204 or of the decrement if in the decreasing mode 208 is decreased (step S360). If fine tuning is to proceed in the direction of the current mode 204, 208 (step S362), the current EA is set to the value of the previous EA (step S364). Processing checks whether the current inc/dec mode is the increasing mode 204 (step S366). If so, the EA is incremented (step S368). If not, the EA is decremented (step S370). In either case, subroutine A is now executed, thereby performing a sector scan. It is checked whether the current GUE is equal to the previous GUE (step S372). If so, processing branches back to the inc/dec mode checking step S366. If, on the other hand, the current GUE is not equal to the previous GUE (step S372), it is checked whether the current GUE exceeds the previous GUE (step S374). If the current GUE exceeds the previous GUE (step S374), return is made, via entry point C, to step S316 in main routine shown in FIG. 3A. Otherwise, if the current GUE does not exceed the previous GUE (step S374), the current EA is set equal to the previous EA (step S376). The current inc/dec mode 204, 208 is switched (step S378), and return is made, via entry point C, to step S316 in the main routine shown in FIG. 3A. Otherwise, if fine tuning is not to proceed in the direction of the current mode 204, 208, but is instead to proceed in the opposite direction (step S362), processing branches forward to the mode switching step S378.

Figure 4:
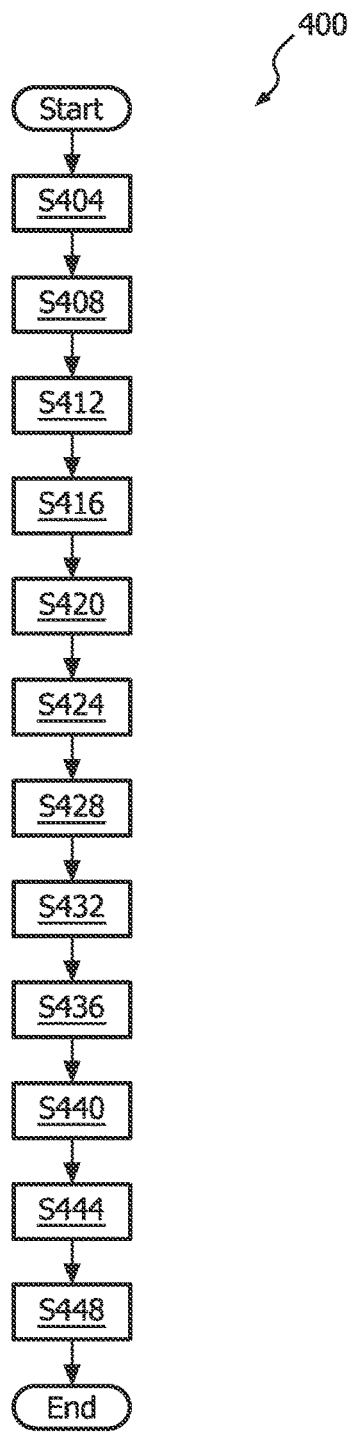
FIG. 4 is a flow chart exemplary of a method for achieving a target in situ ultrasound treatment pressure.

FIG. 4 shows a dose quantifying method 400 for achieving a target in situ treatment pressure. The method for algorithm 300 in FIGS. 3A, 3B and 3C determines a stopping point in the iterations, but reaching the stopping point does not, in itself, tell us what the local in situ pressure is. The dose quantifying method 400 uses an a priori procedure on a phantom to allow clinical determination of the in situ pressure using the afore-described algorithm 300. According to the method 400, phantom vessels 174 are provided (step S404). They are incorporated within a flow phantom 170 (step S408). Microbubbles 172 in a suspension are circulated through the phantom vessels 174 (step S412). A calculation is made of attenuation in the path of the ultrasound to the phantom vessels 174 based on known attenuation coefficients and layer depths (step S416). Applied ultrasound pressure is iteratively increases, sector scan to sector scan until the MGUS is determined (step S420). Local in situ pressure is computed based on the calculated attenuation and the current ultrasound pressure setting (step S424). By applying ultrasound to a patient 116 to now undergo treatment, the algorithm 300 is executed in the preparatory phase (step S428). The current ultrasound pressure setting and the already computed local in situ pressure are used to calculate the current attenuation (step S432). A pressure factor is calculated from the current attenuation (step S436). For example, the current attenuation, in decibels, is divided by 20 and the result is used as a power of 10 to yield the pressure factor. A target in situ pressure for therapy is selected (step S440). The selected pressure is multiplied by the pressure factor to yield an adjusted pressure setting (step S444). An excitation pressure amplitude usable now for therapy is proportional to the adjusted pressure setting (step S448).

An ultrasonic intracranial sonothrombolysis pressure amplitude is pre-quantified by using an ultrasound-scanner control unit having an increasing and/or decreasing mode and designed for: with respect to a current mode, interrogating a blockage site iteratively so as to progressively and respectively increase or decrease a pressure amplitude of ultrasound being emitted to the site at which bubbles for oscillating that is caused by the emitted ultrasound are present; iteration to iteration, deriving, from echoes of the emitted ultrasound, a magnitude of an energy of a signal; and automatically identifying, for the quantifying, an iteration that, in comparison with a just-previous iteration, fails to increase the magnitude. The interrogating may span a region that contains or goes through: the obstruction; another part of the blood vessel; and bubble circulation within a neighboring vessel and a neighboring capillary. The deriving can be based on an ultraharmonic signal, with band-pass filtering being utilized to extract the ultraharmonic signal from returning signals differenced to remove stationary content.

While the invention has been illustrated and described in detail in the drawings and foregoing description, such illustration and description are to be considered illustrative or exemplary and not restrictive; the invention is not limited to the disclosed embodiments.

For example, every few minutes (e.g., every 10 minutes), or at desired intervals, the STL treatment may be temporarily paused, and the algorithm 300 re-executed, to compensate for headset motion or transducer placement, for example.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The word "exemplary" is used herein to mean "serving as an example, instance or illustration." Any embodiment described as "exemplary" is not necessarily to be construed as preferred or advantageous over other embodiments and/or to exclude the incorporation of features from other embodiments. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:
1. An apparatus configured for identifying a pressure amplitude of ultrasound to be applied to a site of the obstruction within a brain for oscillations of bubbles located therein, said apparatus comprising:
an ultrasound-scanner control unit, configured with at least one of an increasing mode and a decreasing mode and configured to control emission of ultrasound to the site of the obstruction to oscillate the bubbles therein, for:
with respect to a current mode from among said at least one, interrogating, by a transducer coupled to the ultrasound-scanner control unit, said site iteratively so as to progressively and respectively increase or decrease at a first interval a pressure amplitude of ultrasound emitted to the site of the obstruction;
iteration to iteration, deriving, by a processor, from echoes of said emitted ultrasound, a magnitude of an ultraharmonic energy signal; and
automatically identifying, by a processor, an iteration, from among the iterations, that, in comparison with a just-previous iteration from among said iterations, fails to increase said magnitude of the ultraharmonic energy signal, thereby identifying the pressure amplitude associated with the site of obstruction beyond the temporal bone;

wherein said pressure amplitude of ultrasound being emitted is an excitation amplitude, said control unit being further configured for, upon said identifying, fine-tuning by: one or both of a) continuing with the iterative interrogating and identifying, using, as a starting point, said excitation amplitude of said just-previous iteration and correspondingly, in accordance with said current mode, continuing to increase or decrease said excitation amplitude progressively with a corresponding increase or decrease at a second interval that is smaller than the first interval used prior to said identifying; and b) continuing with the iterative interrogating and identifying, using, as a starting point, said excitation amplitude of the current iteration and switching over from progressively increasing to progressively decreasing said excitation amplitude, or vice versa, with a corresponding increase or decrease at a third interval that is smaller than the first interval used prior to said identifying.

2. The apparatus of claim 1, said control unit being configured for basing said quantifying, of said pressure amplitude of ultrasound to be applied to said bubbles for the alleviating, upon said magnitude of said just-previous iteration.

3. The apparatus of claim 1, said control unit being configured for, detecting whether a first iteration of excitation amplitude increase, or of excitation amplitude decrease, by virtue of step a) results in a decrease in said magnitude.

4. The apparatus of claim 3, said control unit being further configured for, if said decrease in magnitude is detected, correspondingly switching modes so as to switch over to progressively increasing or progressively decreasing said excitation amplitude in repetition of said interrogating said site and of said identifying for said quantifying.

5. The apparatus of claim 1, said control unit being configured for said interrogating such as to produce ultraharmonic frequencies, for said deriving based on an ultraharmonic signal, and for band-pass filtering to extract said ultraharmonic signal.

6. The apparatus of claim 1, said control unit being configured for filtering out non-ultraharmonic frequency signals conveyed by said echoes to extract an ultraharmonic signal.

7. The apparatus of claim 1, said deriving comprising summing, over an imaging depth dimension, squared values of a signal conveyed from a direction, repeating the summing for signals of multiple corresponding directions, and averaging over said directions.

8. The apparatus of claim 1, said interrogating comprising emitting a pulse having a length 10-40 microseconds long, and said interrogating comprising subsequently emitting, in a same direction as said pulse, a second pulse having a length 10-40 microseconds long, said control unit being configured for computing a difference between respective signals returned by the two pulses.

9. The apparatus of claim 1, said control unit being further configured for said quantifying, and for applying, for the alleviating, ultrasound at an amplitude based on, and no larger than, the quantified amplitude.

10. The apparatus of claim 9, configured for, via a single probe, said interrogating and said applying.

11. A computer readable medium embodying a program having instructions executable by an ultrasound-scanner control unit that cause the ultrasound-scanner control unit to:

interrogating, by a transducer coupled to the ultrasound-scanner control unit, with respect to a current mode from among said at least one, said site iteratively so as to progressively and respectively increase or decrease at a first interval a pressure amplitude of ultrasound being emitted to the site of the obstruction;

iteration to iteration, deriving, by a processor, from echoes of said emitted ultrasound, a magnitude of an ultraharmonic energy; and identifying, by a processor, an iteration, from among the iterations, that, in comparison with a just-previous iteration from among said iterations, fails to increase said magnitude of the ultraharmonic energy signal, thereby identifying the pressure amplitude associated with the site of obstruction beyond the temporal bone;

wherein said pressure amplitude of ultrasound being emitted is an excitation amplitude and said identifying the pressure amplitude associated with the site of obstruction beyond the temporal bone further comprises fine-tuning by: one or both of a) continuing with the iterative interrogating and identifying, using, as a starting point, said excitation amplitude of said just-previous iteration and correspondingly, in accordance with said current mode, continuing to increase or decrease said excitation amplitude progressively with a corresponding increase or decrease at a second interval that is smaller than the first interval used prior to said identifying; and b) continuing with the iterative interrogating and identifying, using, as a starting point, said excitation amplitude of the current iteration and switching over from progressively increasing to progressively decreasing said excitation amplitude, or vice versa, with a corresponding increase or decrease at a third interval that is smaller than the first interval used prior to said identifying.

* * * * *